US011122753B2

(12) United States Patent
Ovadya et al.

(10) Patent No.: US 11,122,753 B2
(45) Date of Patent: Sep. 21, 2021

(54) METHODS FOR MODIFYING FLOWERING TIME AND SEED YIELD IN FIELD CROPS

(71) Applicant: Monsanto Technology LLC, St. Louis, MO (US)

(72) Inventors: Daniel J. Ovadya, Davis, CA (US); Kyle Smith, St. Louis, MO (US); Sheilah Oltmans-Deardorff, Ankeny, IA (US); Rockny Perez, Isabela, PR (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 14/207,284

(22) Filed: Mar. 12, 2014

(65) Prior Publication Data
US 2014/0259905 A1 Sep. 18, 2014

Related U.S. Application Data

(60) Provisional application No. 61/788,709, filed on Mar. 15, 2013.

(51) Int. Cl.
| A01G 22/00 | (2018.01) |
| A01G 7/04  | (2006.01) |
| A01G 7/06  | (2006.01) |
| A01H 3/02  | (2006.01) |

(52) U.S. Cl.
CPC .............. *A01G 22/00* (2018.02); *A01G 7/045* (2013.01); *A01G 7/06* (2013.01); *A01H 3/02* (2013.01)

(58) Field of Classification Search
CPC ........ A01G 7/001; A01G 7/045; A01G 7/067; A01G 7/02; A01H 3/02
USPC ......................... 47/58.1 LS, 58.1 FV, 58.1 R
See application file for complete search history.

(56) References Cited

U.S. PATENT DOCUMENTS

| 2,802,306 | A | * | 8/1957 | Leopold | A01G 7/06 |
| | | | | | 47/58.1 R |
| 4,109,414 | A | * | 8/1978 | Kadkade | A01G 7/045 |
| | | | | | 47/58.1 R |
| 4,371,810 | A | * | 2/1983 | Corth | H01J 61/44 |
| | | | | | 313/487 |
| 4,788,793 | A | * | 12/1988 | Kadkade | A01G 7/045 |
| | | | | | 47/58.1 R |

(Continued)

FOREIGN PATENT DOCUMENTS

| CN | 1094887 A | 11/1994 |
| CN | 101180944 A | 5/2008 |

(Continued)

OTHER PUBLICATIONS

International Search Report and Written Opinion regarding International Application No. PCT/US2014/024626, dated Sep. 16, 2014.

(Continued)

*Primary Examiner* — Ebony E Evans
(74) *Attorney, Agent, or Firm* — Dentons US LLP; David Lanzotti

(57) ABSTRACT

Methods for manipulating yield and generation time of short day plants grown in a field environment are provided. The methods comprise manipulating external signals such as photoperiod in order to increase the per plant seed yield. Also provided are methods for synchronizing the flowering times of plants in different maturity groups.

44 Claims, 9 Drawing Sheets

(56) References Cited

U.S. PATENT DOCUMENTS

| | | | | |
|---|---|---|---|---|
| 4,897,957 | A * | 2/1990 | Oglevee | A01H 3/02 |
| | | | | 47/58.1 R |
| 5,006,154 | A * | 4/1991 | Kaplan | A01H 1/02 |
| | | | | 504/100 |
| 5,269,093 | A * | 12/1993 | Horaguchi | A01G 7/045 |
| | | | | 47/58.1 R |
| 5,525,860 | A * | 6/1996 | Horaguchi | H01J 61/44 |
| | | | | 313/486 |
| 5,718,080 | A * | 2/1998 | Ohtani | A01H 3/02 |
| | | | | 47/58.1 R |
| 5,728,558 | A * | 3/1998 | Fabijanski | A01H 1/02 |
| | | | | 47/DIG. 1 |
| 5,818,734 | A * | 10/1998 | Albright | A01G 9/26 |
| | | | | 700/306 |
| 5,992,090 | A * | 11/1999 | Stutte | A01G 31/00 |
| | | | | 47/58.1 R |
| 6,050,026 | A * | 4/2000 | Ohtani | A01H 3/02 |
| | | | | 47/58.1 R |
| 7,579,150 | B1 * | 8/2009 | Hannapel | C07K 14/415 |
| | | | | 435/6.13 |
| 7,774,979 | B2 * | 8/2010 | Hurst | A01H 3/00 |
| | | | | 47/58.1 LS |
| 7,905,052 | B2 * | 3/2011 | Hurst | A01G 7/045 |
| | | | | 47/29.4 |
| 8,935,880 | B2 * | 1/2015 | Ovadya | A01G 1/001 |
| | | | | 435/410 |
| 9,131,645 | B2 * | 9/2015 | Karpinski | A01G 7/045 |
| 2004/0109302 | A1 * | 6/2004 | Yoneda | A01G 7/045 |
| | | | | 362/2 |
| 2007/0289207 | A1 * | 12/2007 | May | A01G 9/16 |
| | | | | 47/17 |
| 2011/0207615 | A1 | 8/2011 | Ovadya et al. | |
| 2012/0210637 | A1 * | 8/2012 | Kamahara | A01G 7/045 |
| | | | | 47/17 |
| 2013/0007909 | A1 * | 1/2013 | Hildebrand | A01H 5/12 |
| | | | | 800/276 |
| 2015/0143745 | A1 | 5/2015 | Ovadya et al. | |

FOREIGN PATENT DOCUMENTS

| | | |
|---|---|---|
| CN | 101455156 A | 6/2009 |
| CN | 102771286 A | 11/2012 |
| WO | WO 2010/028205 | 3/2010 |

OTHER PUBLICATIONS

U.S. Appl. No. 14/562,489, filed Dec. 5, 2014, Ovadya et al.
Blaney et al., "Inter-relations among the effects of temperature, photoperiod, and dark period on floral initiation of Biloxi soybean," *Bot. Gaz.* 119:10-24, 1957.
Downs et al., "Morphology and reproductive development of soybeans under artificial conditions," *Biotronics* 19:19-32, 1990.
Egli et al., "Temporal profiles of pod production and pod set in soybean," *J. Agronomy* 24:11-18, 2006.
Ellis et al., "Effects of photoperiod and maturity genes on plant growth, partitioning, radiation use efficiency, and yield in soybean [*Glycine max* (L.) Merrill] 'Clark'," *Annals of Botany* 85(3):335-343, 2000.
Guiamet et al., "The effects of long days upon reproductive growth in soybeans (*G. max* L.) cv. Williams," *Japanese Journal of Crop Science* 53(1):35-40, 1984.
Guiamet et al., "Transmission of the long day effects upon reproductive growth and senescence in forked soybean plants cv.," *Phyton* 44(1):37-42, 1984 (abstract).
Hamner et al., "The induction of flowering," *Cornell University Press* 62-89, 1969.
Han et al., "The post-flowering responses of soybean to pre-flowering photoperiodic treatments," *Soybean Science* 14:283-289, 1995 (English abstract).
Han et al., "Phytohormonal Analysis of Some Photoperiod Effects in Soybean," *Acta Agron Sinica* 25(3):349-355, 1999 (English abstract).
Han et al., "Postflowering photoperiod regulates vegetative growth and reproductive development of soybean," *Environmental and Experimental Botany* 55:120-129, 2006.
Jian et al., "Validation of internal control for gene expression study in soybean by quantitative real-time PCR," *BMC Molecular Biology* 9(59):1-14, 2008.
Kantolic et al., "Photoperiod sensitivity after flowering and seed number determination in indeterminate soybean cultivars," *Field Crops Research* 72:109-118, 2001.
Kantolic et al., "Reproductive development and yield components in indeterminate soybean as affected by post-flowering photoperiod," *Field Crops Research* 93:212-222, 2005.
Kantolic et al., "Development and seed number in indeterminate soybean as affected by timing and duration of exposure to long photoperiods after flowering," *Annals of Botany* 99:925-933, 2007.
Raper et al., "Photoperiodic alteration of dry matter partitioning and seed yield in soybeans," *Crop Science* 18:654-656, 1978.
Sysoeva et al., "Photothermal Model of Plant Development," *Russ J. Dev. Bol.* 37(1):16-21, 2006 (English abstract).
Thomas et al., "Photoperiodic control of seed filling for soybeans," *Crop Sci.* 16:667-672, 1976.
Thomas et al., "Morphological response of soybean as governed by photoperiod, temperature and age at treatment," *Bot. Gaz.* 138:321-328, 1977.
USPTO: Office Action regarding U.S. Appl. No. 13/062,507, dated Sep. 24, 2013.
Response to Office Action regarding U.S. Appl. No. 13/062,507, dated Mar. 24, 2014.
USPTO: Final Office Action regarding U.S. Appl. No. 13/062,507, dated Jul. 2, 2014.
Response to Final Office Action regarding U.S. Appl. No. 13/062,507, dated Aug. 26, 2014.
USPTO: Notice of Allowance and Fees Due regarding U.S. Appl. No. 13/062,507, dated Sep. 10, 2014.
USPTO: Non-Final Office Action regarding U.S. Appl. No. 14/562,489, dated Aug. 12, 2016.
Downs et al., "Environment and the Experimental Control of Plant Growth," p. 107, 1975.
Fehr et al., "Stages of Soybean Development," *Special Report 80*, Iowa State University. 1977.
Hess et al., "Effects of rooting volume and nutrient availability as an alternative explanation for root self/non-self discrimination," *Journal of Ecology* 95:241-251, 2007.
Temperatures for St. Louis Science Center (data from Nat'l Centers for Environ. Infor. (http://www.ncdc.noaa.gov/cdo-web/ confirmation), accessed Aug. 5, 2016.
USPTO: Advisory Action regarding U.S. Appl. No. 14/562,489, dated Aug. 2, 2017.
USPTO: Examiner's Applicant-Initiated Interview Summary regarding U.S. Appl. No. 14/562,489, dated Sep. 12, 2017.
Supplemental Response to Final Office Action regarding U.S. Appl. No. 14/562,489, dated Sep. 20, 2017.
Lawrence, "Photoperiodic alteration of reproductive development in soybeans," Dissertation. Iowa State University. 1980.
Office Action regarding Chinese Application No. 2014800143893, dated Oct. 9, 2017.
Response to Non-Final Office Action regarding U.S. Appl. No. 14/562,489, dated Feb. 9, 2017.
USPTO: Final Office Action regarding U.S. Appl. No. 14/562,489, dated May 26, 2017.
Response to Final Office Action regarding U.S. Appl. No. 14/562,489, dated Jul. 7, 2017.
USPTO: Non-Final Office action regarding U.S. Appl. No. 14/562,489, dated Mar. 22, 2018.
Cai et al., "Light intensity-dependent reversible down-regulation and irreversible damage of PSII in soybean leaves," *Plant Science* 163:847-853, 2002.
Response to Non-Final Office action regarding U.S. Appl. No. 14/562,489, dated Jun. 18, 2018.
USPTO: Final Office action regarding U.S. Appl. No. 14/562,489, dated Sep. 28, 2018.
Sirohi et al., "Floral Inhibition in Relation to Photoperiodism in Biloxi Soybean," *Plant Physiology* 37:785-790, 1962.

(56) References Cited

OTHER PUBLICATIONS

Response to Final Office Action regarding U.S. Appl. No. 14/562,489, dated Feb. 19, 2019.
Response to Office Action regarding U.S. Appl. No. 14/562,489, dated Jun. 15, 2020.
Office Action regarding U.S. Appl. No. 14/562,489, dated Feb. 21, 2020.
Han et al., "Studies on the Post-Flowering Photoperiodic Responses in Soybean", (1995), Acta Botanica Sinica 37(11):863-69 (translation only).
Qu et al., Research Progress on Soybean Photoperiod Response Test System, (2010), Soybean Science 29(2):332-35 (translation only).
Parker et al., Effect of Photoperiod on Development and Metabolism of the Biloxi Soy Bean (1939), Int J Plant Sci 100(2):651-89.
Apogee Instruments, https://www,apogeeinstruments.com/conversion-ppfd=to-lux/(2020).
USPTO: Non-Final Office Action Regarding U.S. Appl. No. 14/562,489, dated May 17, 2021.
Borthwick and Parker, Influence of photoperiods upon the differentiation of meristems and the blossoming of Biloxi soy beans, Botanical Gazette 99:825-839; 1938.
Hartung et al., Modifications of soybean plant architecture by genes for stem growth and habit maturity. Crop Science 21(a):51-56, 1981.
Heatherly and Smith, Effect of soybean stem growth habit on height and node number after beginning bloom in the midsouthern USA, Crop Science 44:1855-58, 2004.
Kakiuchi and Kobata, The relationship between dry matter increase of seed and shoot during the seed-filling period in three kinds of soybeans with different growth habits subjected to shading and thinning, Piant Prod. Sci. 9 (1):20-26, 2006.
Kato et al., Effect of change from a determinate to a semi-determinate growth habit on the yield and lodging resistance of soybeans in the northeast region of Japan, Breeding Science 69:151-159, 2019.
Tian et al., Artificial selection for determinate growth habit in soybean, PNAS 107(19):8563-68. 2010.
Ziska at al., Rising atmospheric carbon dioxide and seed yield on Soybean genotypes, Crop Science 41(2):385-391, 2001.

\* cited by examiner

METHODS FOR MODIFYING FLOWERING TIME AND SEED YIELD IN FIELD CROPS

CROSS REFERENCE TO RELATED APPLICATIONS

This application claims the benefit of U.S. Provisional Application No. 61/788,709 filed Mar. 15, 2013, herein incorporated by reference in its entirety.

FIELD OF THE INVENTION

The present invention relates to the fields of plant breeding and crop science. More specifically, the present invention relates to methods for manipulating flowering and seed yield of plants grown in a field.

BACKGROUND OF THE INVENTION

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. It may take many generations of breeding to obtain desired outcomes, the success of which could be complicated by factors such as different modes of inheritance, the effectiveness of screening, and differential flowering times, among many others.

Soybean (*Glycine max*) is a photoperiodic plant that is widely grown for its bean, which has a large number of uses. The typical phenology of full-season soybean begins with an extended period of vegetative growth. The vegetative stages begin with unifoliate stage (V0) and continue with V1, V2, V3, V4, etc., as each new trifoliate leaf is expanded, so that a V2 plant has an expanded V2 trifoliate leaf, a V3 plant has an expanded V3 trifoliate leaf, and so on. With a typical planting date of May $1^{st}$ in North America, the vegetative period of soybean growth lasts from 55-65 days. The reproductive phase, referred to as R1, begins with the presence of a flower at any node on the plant, which occurs in mid July for most adapted soybean maturities grown in a North American field environment. Reproductive development continues through 50% flowering, end of flowering, seed filling, and seed ripening.

BRIEF SUMMARY OF THE INVENTION

In one aspect, the invention provides a method for increasing seed yield in a field-grown plant. In one embodiment, the method comprises the steps of: (a) growing a plant in a field under vegetative conditions; (b) exposing a juvenile plant to a floral induction treatment to initiate flowering; and (c) returning the plant to vegetative growing conditions. In certain embodiments, the vegetative growing conditions of part (a) and (c) are provided by the use of artificial lighting. In specific embodiments the floral induction treatment is an early treatment. Artificial lighting may, in particular embodiments, be provided to the plant before sunrise. In some embodiments, the plant is a photoperiodic short day plant. Non-limiting examples of types of plants that may be used in the method include soybean, cotton, rice, sorghum, maize, sugarcane, tobacco, canola, alfalfa, strawberry, wheat, barley, and tomato. In one embodiment, the plant is a soybean plant.

In specific embodiments, a method of the invention comprises a floral induction treatment comprising about 10 to 14 hours of darkness per night, including about 10.5 to about 14, about 11 to about 14, about 12 to about 14, about 10 to about 13.5, about 10 to about 13, or any other range derivable therefrom. In other embodiments, a method of the invention comprises a floral induction treatment maintained for a period of about 3 to about 28 days, including about 3 to about 25, about 3 to about 20, about 3 to about 14, about 10 to about 28, about 10 to about 20, about 10 to about 14, about 14 to about 28, about 14 to about 21, and about 20 to about 28 days. In another embodiment, the floral induction treatment is initiated at a growth stage of from about VE to about V4, including any of VE, V1, V2, V3, or V4. In yet another embodiment, a method of the invention comprises vegetative growing conditions of from about 14 to about 24 hours of light per day, including about 14, 15, 16, 17, 18, 19, 20, 21, 22, 23 or 24 hours per day and any ranges derivable therein, including from about 14 to about 20 hours, from about 14 to about 18 hours and from 16 to about 18 hours. In a further embodiment, a method of the invention comprises vegetative growing conditions including exposing a plant to artificial light with an intensity of at least about 2 µmoles/m·s, including from a lower intensity of at least about 2, 5, 10, 15, 20, 25, 35, 50, 100, 200, 300, or 500 µmoles/m·s or more. In certain embodiments, the artificial light is defined as having an intensity of less than about 5, 10, 15, 25, 50, 75, 100, 150, 250, 400, 500, 750 or 1,000 µmoles/m·s. In specific further embodiments, a method of the invention comprises growing a plant under conditions that restrict vegetative growth and enhance flowering. In still further embodiments, one or both of part (a) and part (c) comprise providing about 1, about 2, about 3, about 4, or about 5 hours of artificial light before sunrise.

In another aspect, the invention provides a method for manipulating flowering time in a plurality of field-grown plants. In one embodiment, the method comprises the steps of (a) initiating growth of a plurality of plants under vegetative growing conditions; (b) growing the plants under a floral induction treatment to initiate flowering; and (c) returning the plants to vegetative growing conditions. In the method, vegetative growing conditions of one or both of part (a) or (c) may be provided by the use of artificial lighting. In a particular embodiment, the artificial lighting is provided before sunrise. In other embodiments, the artificial lighting may comprise an intensity of at least about 2, 5, 10, 15, 25 or 50 µmoles/m·s, in other embodiments, the artificial light may comprise an intensity of less than about 50, 75, 100, 150, 250, 500, or 1,000 µmoles/m·s. In another embodiment, the plurality of plants comprises plants of at least two different genotypes, including different maturities. The plants may in one embodiment all be of the same species. In certain further embodiments, the method synchronizes the flowering time of said plants of at least two different genotypes to permit crossing the plants. In still further embodiments, the plurality of plants comprises a photoperiodic short day plant.

In still yet other embodiments a plurality of plants in a method of the invention comprises soybean, cotton, rice, sorghum, maize, sugarcane, tobacco, canola, alfalfa, strawberry, wheat, barley or tomato plants. In one embodiment the plurality of plants comprises soybean plants. In one embodiment, floral induction treatment conditions of part (b) comprise about 11 to about 13 hours of darkness per night. The floral induction treatment of part (b) may be maintained, in specific embodiments, for about 7 to about 28 days, including about 7, 10, 12, 14, 17, 20, 23, 26 and 28 days. In other embodiments, a plant in any of steps (a) to (c) is defined as at a growth stage of from about VE to about V4, including any of about VE, V1, V2, V3 and V4. In other embodiments, vegetative growing conditions of one or both of part (a) and part (c) comprise from about 14 to about 18 hours of light per day, and in still other embodiments, one or both of part (a) and part (c) comprise providing about 1, about 2, about 3, about 4, or about 5 hours of artificial light before sunrise. The method may also further comprise growing the plurality of plants under conditions that restrict vegetative growth and enhance flowering, and at least two of said plurality of field-grown plants are planted at differing times.

In still yet another aspect, the invention provides a method for increasing seed yield in a soybean plant, the method comprising: (a) exposing a soybean plant in a field to vegetative growing conditions with the use of artificial lighting; (b) growing the plant under a floral induction treatment of 3-28 days in duration to initiate flowering, wherein said floral induction treatment is initiated at a growth stage of from about VE to about V4, and wherein said floral induction treatment comprises about 10 to about 14 hours of darkness per night; and (c) returning the plant to vegetative growing conditions of 14-60 days in duration, wherein said vegetative growing conditions comprise providing artificial lighting before sunrise to expose the plant to from about 10 to about 16 hours of light per day. In one embodiment of the method, the artificial lighting may comprise an intensity of at least about 2, 5, 10, 15, 25 or 50 µmoles/m·s. In other embodiments, artificial lighting comprises an intensity of less than about 50, 75, 100, 150, 250, 500, or 1,000 µmoles/m·s.

Another embodiment relates to a method for increasing seed yield in a field-grown plant comprising the steps of: (a) initiating growth and growing a plant in a field under a floral induction treatment to initiate flowering; and (b) exposing the plant to vegetative growing conditions. In another aspect, a method for manipulating flowering time in a plurality of field-grown plants comprises the steps of (a) initiating growth and growing a plurality of plants under a floral induction treatment to initiate flowering; and (b) exposing the plants to vegetative growing conditions, is provided. In certain embodiments, the vegetative growing conditions of part (b) are provided by the use of artificial lighting. In still further embodiments, part (b) comprises providing about 1, about 2, about 3, about 4, or about 5 hours of artificial light before sunrise.

In another aspect, the invention provides a method of growing a plant comprising: (a) initiating growth of at least a first plant in a field; (b) determining the natural photoperiod of the field grown plant; (c) adjusting the photoperiod to which the field grown plant is exposed with an artificial light source to produce a vegetative growing condition; (d) growing a plant in a field under vegetative growing conditions to a juvenile stage; (e) exposing the juvenile plant to a floral induction treatment, such that a flowering response is initiated; (f) adjusting the photoperiod to which the field grown plant is exposed with an artificial light source to produce a vegetative growing condition; and (g) growing the plant under vegetative growing conditions.

In another aspect, the invention provides a method of growing a plant comprising: (a) initiating growth of at least a first plant in a field; (b) determining the natural photoperiod of the field grown plant; (c) growing the plant under natural photoperiodic conditions to provide a floral induction treatment, such that a flowering response is initiated; (d) adjusting the photoperiod to which the field grown plant is exposed with an artificial light source to produce a vegetative growth condition; and (e) growing the plant under vegetative growing conditions.

In still another aspect, the invention provides a method of growing a plant comprising: (a) initiating growth of at least a first plant in a field; (b) determining the natural photoperiod of the field grown plant; (c) growing the plant under vegetative growing conditions; (d) adjusting the photoperiod to which the field grown plant is exposed to provide a floral induction treatment, such that a flowering response is initiated; and (e) returning the plant to vegetative growing conditions.

Figure 7:
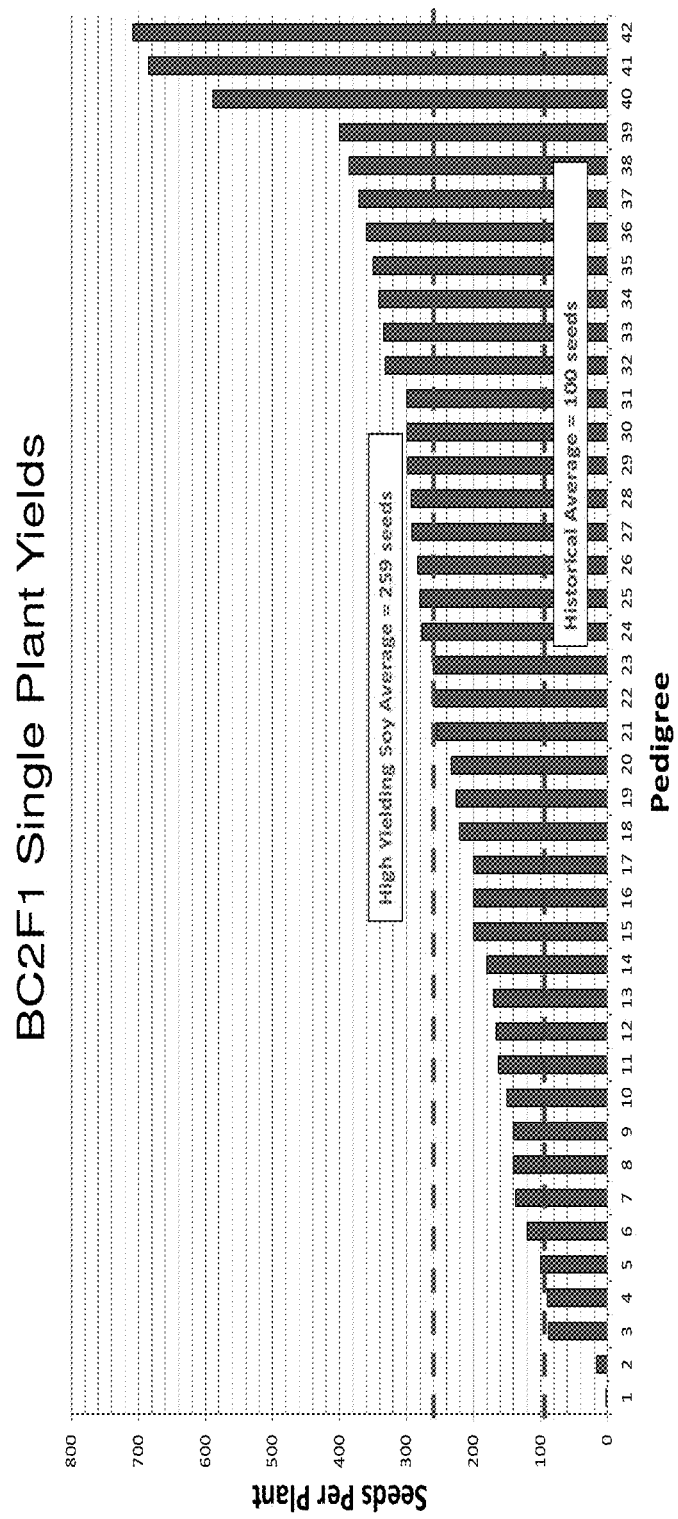

FIG. 7: Shows increased average single plant yield and percentage of plants reaching 100 seeds with the floral induction treatment. The plant high yield phenotype is consistent with the treatment received.

Figure 8:
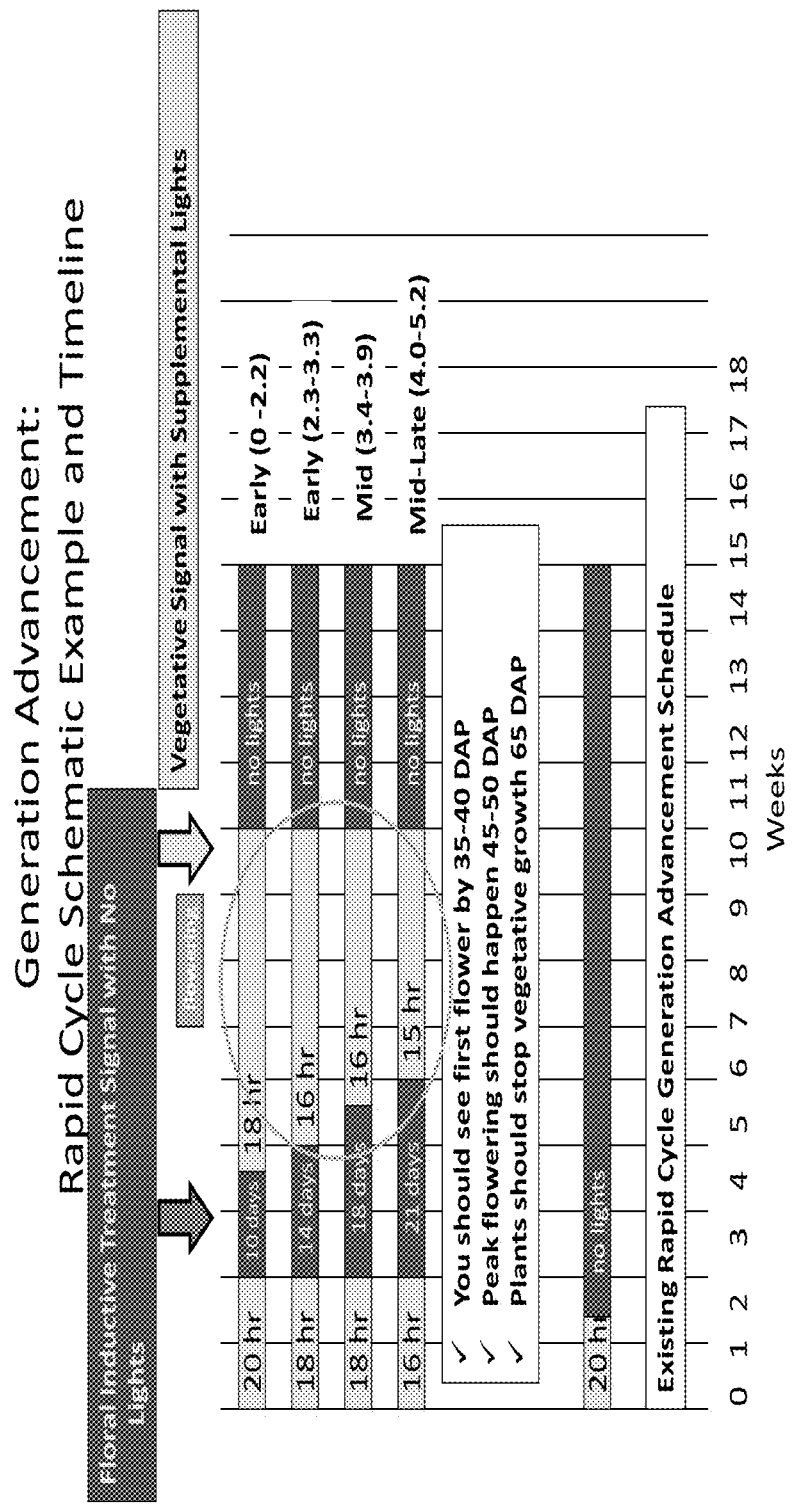

FIG. 8: Shows a treatment schematic of application of the floral induction treatment at the juvenile phase to induce early flowering in a 100-day cycle. It also shows how the floral induction treatment is customized for mega-maturity groups with later maturity groups receiving more floral induction dosage to achieve persistent flowering response under the vegetative photoperiod. The historical method uses the vegetative signal to delay flowering and this shortens the flowering phase.

Figure 9:
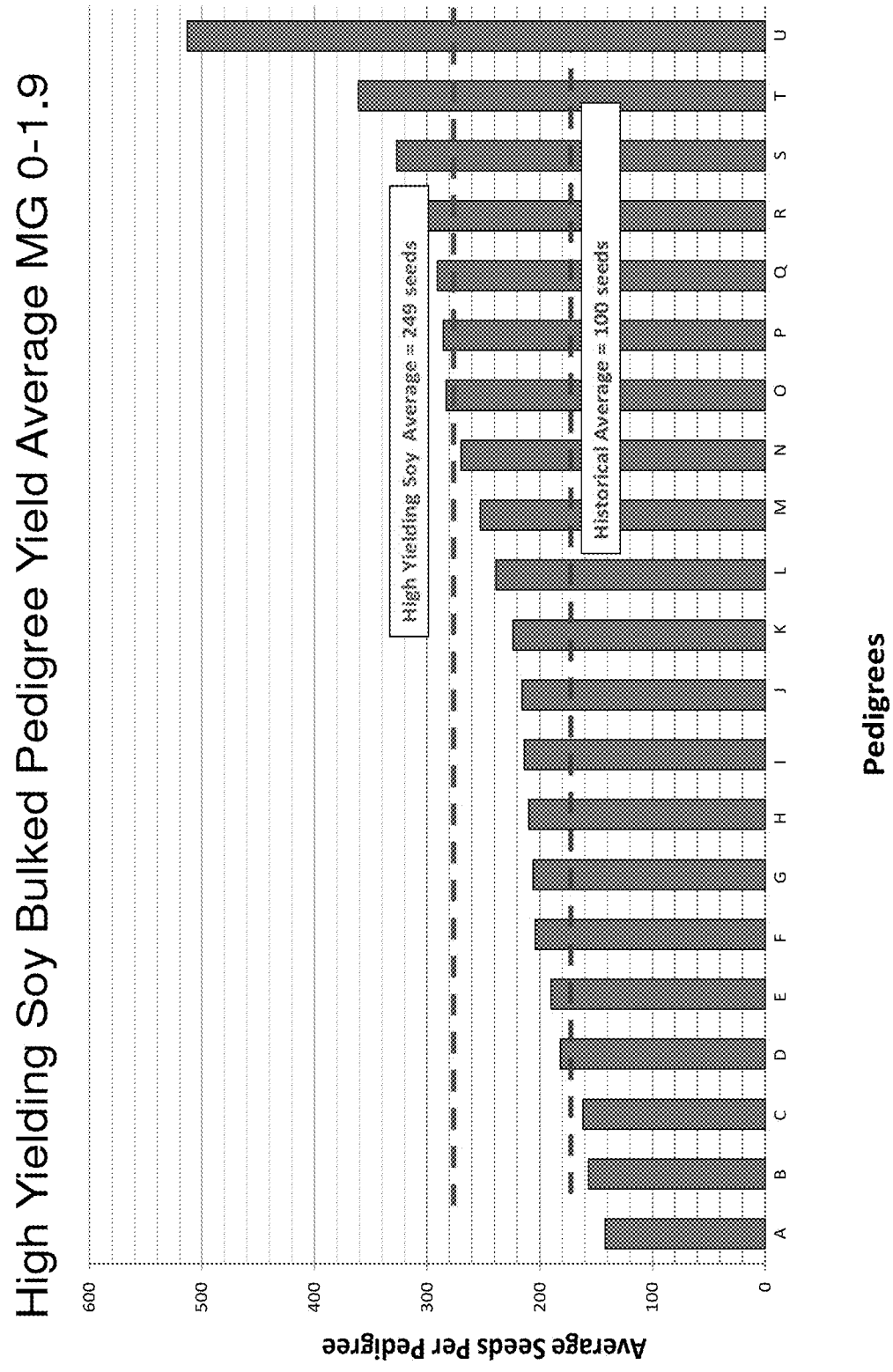

FIG. 9: Shows the average yields across bulked up pedigrees. The floral induction treatment more than doubles the average seeds per pedigree.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

Definitions

Unless otherwise defined, all technical and scientific terms used herein have the same meaning as commonly understood by one of ordinary skill in the art. Where a term is provided in the singular, the plural of that term is also contemplated unless otherwise indicated. Where there are discrepancies in terms and definitions used in references that are incorporated by reference, the terms used in this application shall have the definitions given herein.

In the description that follows, a number of terms are used extensively. The following definitions are provided to facilitate understanding of the present embodiments.

As used herein, the term "photoperiod" means the duration of light exposure in a 24-hour period. The term "natural photoperiod" means the normal day length at a particular location on a particular date. The natural photoperiod may be altered by the use of artificial lighting or coverings that block light exposure.

As used herein, the phrase "floral induction treatment" means exposing a plant to a photoperiod length that induces a flowering response.

As used herein, the phrase "vegetative growing conditions" means a photoperiod length sufficient to promote vegetative growth and repress reproductive maturation.

As used herein, a "cycle" refers to one day of exposure to a given photoperiod length.

As used herein, a "V" or a "V stage" refers to a vegetative stage of growth in a plant. For example, as used herein, "Ve" or the "Ve stage" refers to the emergence of a plant from the surface of the soil; "V1 or the "V1 stage" is when the first set of trifoliate leaves are unfolded; "V2" or the "V2 stage" is when the first trifoliate leaf is fully expanded in a plant; "V3" or the "V3 stage" is when the second trifoliate leaf is fully expanded; and "V4" or the "V4 stage" is when the third trifoliate leaf is fully expanded. A plant according to the present invention may be of any V stage, including VE, V1, V2, V3, V4, V5, or the like. This system is well known to those of skill in the art.

As used herein, "vigor" or "plant vigor" refers to a measure of plant growth or foliage volume, stem size, and root development. For example, a V3 plant with low vigor may be equivalent to a V2 plant with good vigor. Plants seeded on the same day usually have different development rates. For example, a control plant may take 11 days after seeding to reach V2, while some R1 transgenic seeds may take 21 days to reach V2 stage.

As used herein, the term "variety" means a group of similar plants that by their genetic pedigrees and performance can be identified from other varieties within the same species.

The term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and to "and/or."

When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Generally, the nomenclature used herein and the manufacture or laboratory procedures described below are well known and commonly employed in the art. Conventional methods are used for these procedures, such as those provided in the art and various general references. The inventors do not intend to be limited to a mechanism or mode of action. Reference thereto is provided for illustrative purposes only.

DESCRIPTION

The embodiments described herein relate to methods for increasing the seed yield of a field-grown plant by manipulating the timing and duration of flowering and vegetative growth phases of a field-grown plant. Also described are methods for manipulating (e.g., synchronizing) flowering time in a plurality of field-grown plants, including plants of multiple maturity groups. In certain applications, a floral induction (short day) photoperiod treatment is provided to field-grown plants at the juvenile phase to induce flowering, followed by a long day photoperiod treatment to stimulate vegetative growth while prolonging the flowering response. In certain embodiments, day length of plants grown in a field may be altered through supplementation with artificial lights or by covering to block light exposure.

Several embodiments of the invention relate to a method comprising: (a) initiating growth of at least a first plant under vegetative growing conditions; (b) controlling the environment of the plant to provide for a period of floral induction growing conditions, such as, for example, about 3 to about 28 days; and (c) resuming vegetative growing conditions following the period of floral induction treatment growing conditions.

Several embodiments of the invention relate to a method comprising: (a) initiating growth of at least a first plant in a field; (b) determining the natural photoperiod of the field grown plant; (c) adjusting the photoperiod to which the field grown plant is exposed with an artificial light source to produce a vegetative growing condition; (d) growing a plant in a field under vegetative growing conditions to a juvenile stage; (e) exposing the juvenile plant to a floral induction treatment, such that a flowering response is initiated; (f) adjusting the photoperiod to which the field grown plant is exposed with an artificial light source to produce a vegetative growing condition; and (g) growing the plant under vegetative growing conditions.

Several embodiments of the invention relate to a method comprising: (a) initiating growth of at least a first plant in a field; (b) determining the natural photoperiod of the field grown plant; (c) growing the plant under natural photoperiodic conditions to provide a floral induction treatment, such that a flowering response is initiated; (d) adjusting the photoperiod to which the field grown plant is exposed with an artificial light source to produce a vegetative growth condition; and (e) growing the plant under vegetative growing conditions.

Several embodiments of the invention relate to a method comprising: (a) initiating growth of at least a first plant in a field; (b) determining the natural photoperiod of the field grown plant; (c) growing the plant under vegetative growing conditions; (d) adjusting the photoperiod to which the field grown plant is exposed to provide a floral induction treatment, such that a flowering response is initiated; and (e) returning the plant to vegetative growing conditions.

Plants having different genotypes can mature at different rates, and differences in flowering time can prevent cross pollination, even when the plants are planted at the same time. Several embodiments described herein relate to a method of promoting cross pollination between two or more plants having varying maturity levels, wherein flowering is synchronized. In some embodiments, the plants are planted at the same time. In other embodiments, the plants are planted at different times. In certain embodiments, plants of at least two different genotypes are planted with divergent maturities and thus, under normal conditions, may flower at times that may prevent cross pollination. The present invention thus overcomes limitations in the prior art by enabling better synchronization of flowering in a group of plants at varying maturity levels, even when the plants are planted at the same time. In an embodiment of the invention, such a group of plants may comprise plants of at least 2, 3, 4, or more different maturities in a single field, or in pollinating proximity. In one embodiment, one or both plants to be synchronized may be planted at a latitude to which it is not adapted. Notably, in plants at divergent maturity groups the flowering signal initiated in response to a floral induction treatment in accordance with the present methods may be persistent even after resuming vegetative growth conditions after floral induction treatment.

In some embodiments, vegetative growth-inducing (long day length) conditions may be provided to the plants with the use of artificial lights. Non-limiting examples of artificial lighting include, the use of a 1000-watt metal halide portable light tower placed over the plants. Other types of light such as high pressure sodium or LED may be provided, as well. In some embodiments, vegetative growth conditions may be providing to a field-grown plant by extending the natural day length through exposing the field-grown plant to artificial light before dawn (pre-dawn lighting) and/or exposing the field-grown plant to artificial light from dusk to sometime later in the night (continuation lighting, also called day-extension lighting). Day length may be artificially extended for about 1 hour, 2 hours, 3 hours, 4 hours, 5 hours, or 6 or more hours. In other embodiments, vegetative growth conditions may be provided to a field-grown plant by exposing the field-grown plant to artificial light during the night (night interruption lighting). With night interruption lighting, a field-grown plant may be exposed to artificial light about 1 hour into the dark period, about 2 hours into the dark period, about 3 hours into the dark period, about 4 hours into the dark period, about 5 hours into the dark period, about 6 hours into the dark period, about 7 hour into the dark period, about 8 hours into the dark period, about 9 hours into the dark period, or about 10 or more hours into the dark period, and exposure to artificial light may last for about 30 seconds, about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, about 35 minutes, about 40 minutes, about 45 minutes, about 50 minutes, about 55 minutes, about 1 hour, about 1.5 hours, about 2 hours, or about 3 or more hours. In some embodiments, a field-grown plant is exposed to artificial light 1, 2, 3, 4, 5, 6, 7, 8, 9, 10 or more times during the night.

In certain embodiments, vegetative growth conditions are provided by artificial light added before dawn, referred to as "night interruption." When vegetative growth conditions are provided by a "night interruption" signal, the plant is transitioned from total darkness to supplemental light to natural light. Plant response to artificial lighting provided before dawn rather than after sunset may be used to provide surprising beneficial results, such that the plants exhibit enhanced vegetative vigor, enhanced flowering and/or increased seed production.

Without being held to a particular theory, resumption of vegetative growing conditions after a period of floral induction treatment that induces flowering may send a vegetative signal to already reproductive plants, and result in increased branching, shorter internodes, reduced shading, and more pods per internode. The methods described herein solve a variety of seed production concerns and can be utilized in the research, regulatory, breeding, and commercial phases of product development. For example, the amount of seeds produced and the amount of time required to produce such seeds can be varied depending on the need in a particular product development phase. Utilizing the methods described herein, it is possible to increase per-plant seed yield and simultaneously synchronize flowering times of different plants of different maturity groups. It is also possible to increase the number of plants producing at least a desired minimum number of seeds. This provides ease in plant breeding by enabling breeders to produce crosses of plants of multiple maturities that would normally not be possible due to temporal reproductive isolation. In another embodiment, such a method provides a way for researchers and growers to mass pollinate plants in both field and controlled environments. These advantages to the breeding process can ultimately lead to faster launch of any commercial trait and more rapid adoption of commercial traits in the marketplace compared to the historical method.

Certain embodiments relate to modification of the photoperiod of plants in a field setting through the use of artificial lights applied before dawn. In one embodiment, a soybean plant may be manipulated to produce an increased yield of seeds in a required time for a specific project. This may be useful to speed development time for new varieties or introduction of new traits, which is essential given the number of years that may be involved in a given breeding program.

In a particular application of the methods described herein, increasing the amount of seeds produced from a single plant can reduce the amount of work required for molecular characterization of pure seeds for commercial testing and production. For example, 12-18 sibling lines are traditionally bulked to create a commercial seed lot with confirmed genetic purity. However, using the methods described herein, only one or two plants may be needed to produce a commercial seed lot, thus significantly reducing the amount of quality assurance and/or quality control assays required on sibling lines. Increasing the amount of seeds produced from a single plant may also be beneficial so that archiving, biochemical analyses e.g., oil and fatty acid analyses, and germination studies can be completed using seeds from a single plant thus reducing the variation in source material when more than one plant is used.

In another embodiment, further benefits of the present invention can be achieved by producing more developing pods from a single plant. More developing pods provide for more immature embryos, which in turn can supply the relatively large amounts of protein normally required for conducting studies for regulatory dossier.

Producing more seeds from a single plant may further enable the identification of more progeny seeds with an acceptable molecular profile, e.g., seeds with single copy inserts without the vector backbone expressing a gene of interest at an efficacious level, from plants transformed with 2T constructs or multiple-traits where the probability of finding a desired seed is lower in a population of seeds. For example, only 1 out of 256 seeds is likely to contain a triple homozygous marker-free plant. With a large number of seeds produced from a single plant, it is easier to identify such a seed. Increased single plant yield at the F2 generation also reduces the need to make large amounts of F1 seed thereby saving large amounts of land and time performing hand pollinations.

Several embodiments described herein relate to a method of hybridizing a soybean variety of maturity group 000 and a soybean variety of Maturity group X, comprising co-planting one or more soybeans of Maturity group 000 and one or more soybeans of Maturity group X. Soybean varieties have a wide maturity range, from maturity group 000 (very early) to X (very late) and thus hybridization between varieties of divergent maturities is difficult. In many cases, the receptivity of the female flower does not coincide with the availability of pollen from the male parent. Traditionally, this means that complex sequential plantings that require extensive land usage must be performed in order to ensure that flowers would be available from both parents to be used in hybridization. The ability to induce simultaneous flowering in a group of plants as described herein therefore may provide growers with new hybridizations that traditionally were not possible. In addition, using the artificial lighting methods as provided herein may be useful to equalize plant height among plants of different maturities such that growth of vegetative and reproductive structures is controlled, allowing the light better access to flower buds and better penetration into the plant canopy and a reduction in pod abscission. Control of plant height and leaf canopy reduces plant to plant competition for light at field densities and subsequent plant lodging and loss of material.

The methods described herein may further reduce generation time, which can enable rapid advancement of a seed to meet specific field planting deadlines, obtain acceptable molecular profiles and sufficient seed yields, and provide improved efficiency of large grow-outs due to high plant density. Without being held to a particular theory, experience to date suggests that the methods described herein appear to disrupt, enhance, or compete with a plant's normal circadian rhythm to trigger early flowering in physiologically young plants. By delivering a more effective vegetative signal with circadian entrainment and extension of the dark-light transition (i.e. dawn), such a method may enhance yield by inducing indeterminate flowering, more branching, shorter internodes, and more flowers and pod set per internode.

The methods of the present invention allow a grower to customize the seed yield and generation time to meet specific business needs. Single plant yields may be increased by 20 fold (2000%) or more by using this method in the equivalent cycle time as the historical method. The yield distribution of a large field plot may also be improved so that over 95% of the single plants achieve or exceed the minimum yield target. In an embodiment of the invention, utilizing the described lighting schemes in breeding nursery fields may enable growers to eliminate a backcross (BC) step, such as the 3F4 generation, in Marker Assisted Back Crossing (MABC) nurseries. Elimination of such steps may lead to new yield testing in a more timely fashion by, for example, an increased BC3F1, BC3F2, and BC3F4 yield (resulting in a 200 to 300% increase). Utilizing the described growing methods, in conjunction with pollen preservation, may therefore result in more pollen production per donor plant more consistently in MABC crossing blocks. The top two genotypic plants may then be selected as donors to make the next round of back crosses, rather than the typical practice, in which ten donor plants are used due to the limited amount of pollen. Historical data indicates that successful lines come from donor 1 or 2 greater than 90% of the time. This invention may produce single male donor plants that produce 1000 or more flowers with viable pollen and continuous flowering for 100 days or longer. This would make the process more efficient.

The methods described herein may enable field trials to be conducted in a single location several months faster than the seeds produced with the current short day methods. Current short day methods require an extra seed increase generation step in the field to obtain sufficient seeds for conducting a field trial in one location in a subsequent year. The time savings of several months could lead to earlier commercial launch dates and ultimately additional product revenues.

In accordance with the present invention, vegetative growing conditions may comprise, for example, at least about 14 hours of light, including at least about 14, 15, 16, 17, 18, 19, 20, 21, or 22 or more hours of light per day. In certain embodiments of the invention, an artificial light intensity may range from about 0.13 µmoles/m·s to about 450 µmoles/m·s, including about 0.13, about 0.15, about 0.20, about 0.25, about 0.30, about 0.40, about 0.50, about 1, about 2, about 3, about 4, about 5, about 10, about 15, about 20, about 30, about 40, about 45, about 50, about 60, about 70, about 80, about 90, about 100, about 150, about 200, about 250, about 300, about 350, about 400, about 410, about 415, about 420, about 425, about 430, about 435, about 440, about 445, about 446, about 447, about 448, about 449, about 450, or more µmoles/m·s.

In one embodiment, 1000-W metal halide bulbs with less than 6000 hours of run time may be used for experiments to produce output equal to 80% of their maximum lumen. The average SLC intensity estimate for two 1000-W metal halide bulbs over the 5000 ft2 field may be 7.6 μmoles/m²/s, while the minimum SLC intensity may be 1.0 μmoles/m²/s, and the maximum SLC intensity may be 33 μmoles/m²/s.

In another embodiment, 1000-W metal halide bulbs may exhibit a spectrum output comprising a balance of red and blue wavelength light within the photosynthetically active range (PAR) of 400-700 nanometers. Based on controlled environment testing with day length treatments, literature, and MSP field data, other high-intensity discharge lights with sufficient PAR intensity may be expected to recapitulate the yield response, including high pressure sodium and light emitting diodes.

Floral induction treatment conditions range from 10-14 hours and may be provided in certain embodiments, for example, for about 5, 6, 7, 8, 9, 10, 11, 12, 13, 14, 15, 16, 17, 18, 19, 20, 21, 22, 23, 24, 25, 26, 27, 28, 29, or 30 days to induce flowering. The period of floral induction treatment may be initiated, for example, at a plant growth stage of from about VE to about V4, including at the VE stage, V1 stage, V2 stage, V3 stage and V4 stage. Younger plants (i.e. plants at a lower plant growth stage) may respond more readily to floral induction treatment than older plants. Thus, in one embodiment, plant varieties that exhibit an indeterminate growth pattern may respond more favorably to floral induction conditions at the V2 plant growth stage, while varieties that exhibit a determinate growth pattern may respond more favorably to floral induction treatment at the V4 stage. In an embodiment of the invention, the floral induction treatment may comprise maintaining from about 10 to about 14 hours of darkness per night, including about 10, about 11, about 12, about 13, or about 14 hours of darkness per night.

Plants useful in accordance with the present invention may be a short day or day neutral or long day plant. A short day plant may include, but is not limited to, soybean, cotton, rice, sorghum, maize, sugarcane, tobacco, canola, alfalfa, strawberry, wheat, barley, and tomato. Plants able to be used according to the method may be in any maturity group, i.e. Group 1, Group 2, Group 3, Group 4, Group 5, or the like.

In Southern latitudes, days are shorter than "normal" for soybean and thus, supplemental lights may be used in Northern latitudes to prevent flowering. In the absence of supplemental lighting in Northern latitudes, soybean plants flower too quickly and the plant size remains very small. Thus, in an embodiment of the invention, a shorter day length than "normal" may be used to induce the plant to flower early by turning lights off to provide a floral induction treatment and then turning supplemental lights back on to provide vegetative growing conditions. Such a lighting method to produce a high yielding phenotype is contemplated herein.

The duration of floral induction treatment establishes the reproductive dose in the plant, with more floral induction treatment cycles creating a greater flowering response and faster life cycle time. The methods described herein change normal soybean phenology and decouple flowering time from maturity by using light signals to trigger overlapping vegetative and reproductive growth responses. Plants may become receptive to floral induction treatment signal at the unifoliate stage and may become less sensitive to floral induction treatments as they develop over time. For example, a one-week floral induction treatment of a V2 plant will create more induction than a similar one-week floral induction treatment on a V5 plant. Thus, not to be bound by a particular theory, floral induction treatment may create a dose-dependent, mobile signal that may be established in all plant tissues so that older plants, which have more leaf tissue, may require a greater floral induction signal to establish an equivalent reproductive dosage. The strength and persistence of the flowering response is established with floral induction treatment. Several embodiments described herein are related to a method for decreasing life cycle time, comprising exposing a plant to a greater number of floral induction treatment cycles, thereby providing a stronger and more permanent flowering dose. Other embodiments described herein are related to a method for increasing seed yield, comprising exposing a plant to fewer floral induction treatment cycles, thereby providing a weaker flowering dose and a prolonged reproductive phase. In an embodiment of the present invention, the duration of floral induction treatment may be altered to create a range of seed yield and time to maturity. The duration of floral induction treatment may also be modified to obtain the correct flowering response in a broad range of maturity groups with different sensitivities to floral repression. Thus, a temporary reproductive treatment may be beneficial in order to trigger the correct and permanent changes in plant development.

EXAMPLES

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

Example 1

Full Cycle Generation Advancement

Figure 1:
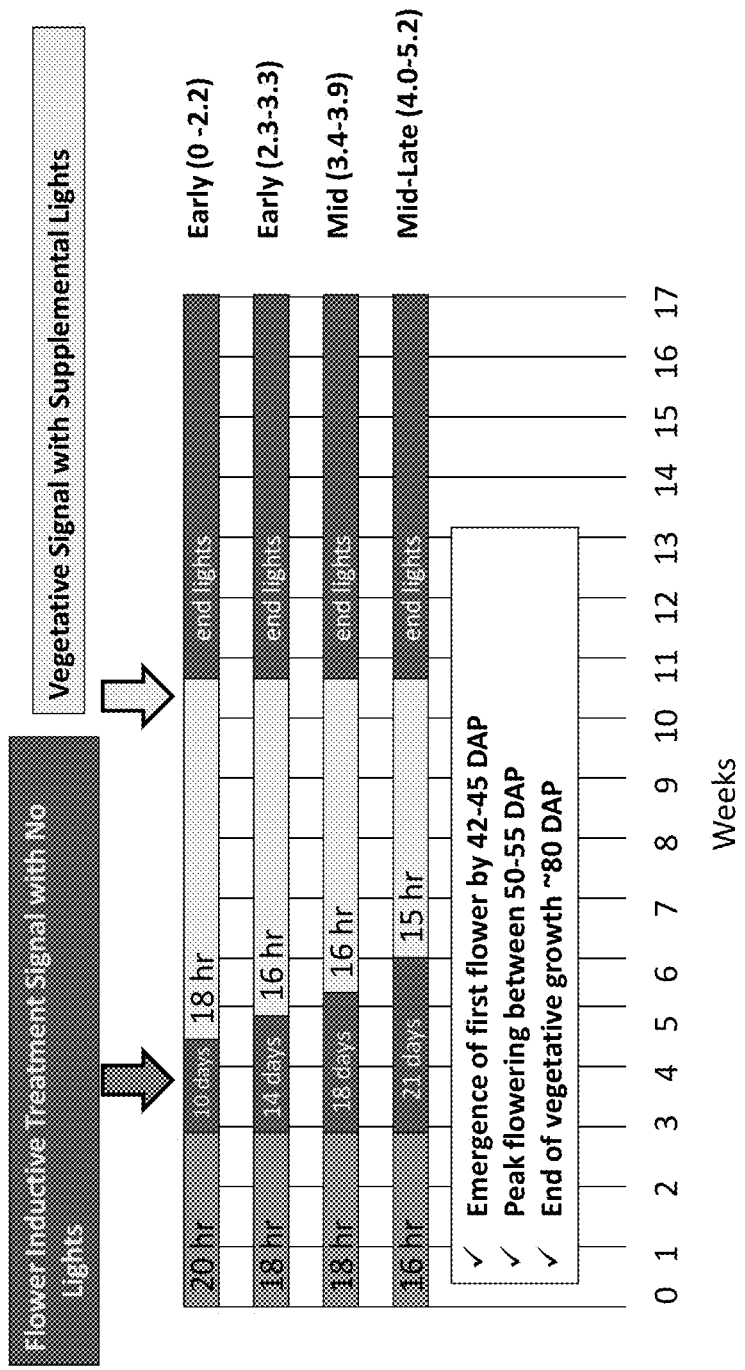
FIG. 1: Shows a graph of the Full Cycle Generation Advancement to induce flowering in juvenile soybean in a 120 day cycle. For full cycle generation advancement of soybean, plants are typically grown under vegetative conditions to the V0-V3 stage before floral induction treatment. The duration of the floral induction treatment is extended for later maturity groups to obtain a higher reproductive dosage than earlier maturity groups. In addition, the pre- and post-floral treatment vegetative photoperiod is customized for each maturity group to ensure the reproductive dose is persistent. Following floral induction treatments plants are returned to a vegetative state supplemented with artificial lighting.

Juvenile Soy plants (V0-V4) grown in field conditions were grown under vegetative conditions to the V0-3 stage before floral induction treatment (FIG. 1.). The duration of the treatment is extended for later maturity groups to obtain a higher reproductive dosage than earlier maturity groups. In addition, the pre- and post-treatment vegetative photoperiod is customized for each maturity group to ensure the reproductive dose is persistent. After floral induction, the plants are returned to vegetative growth. The Vegetative Signal is provided by means of supplemental lights before dawn.

Example 2

Night Interruption

Figure 2:
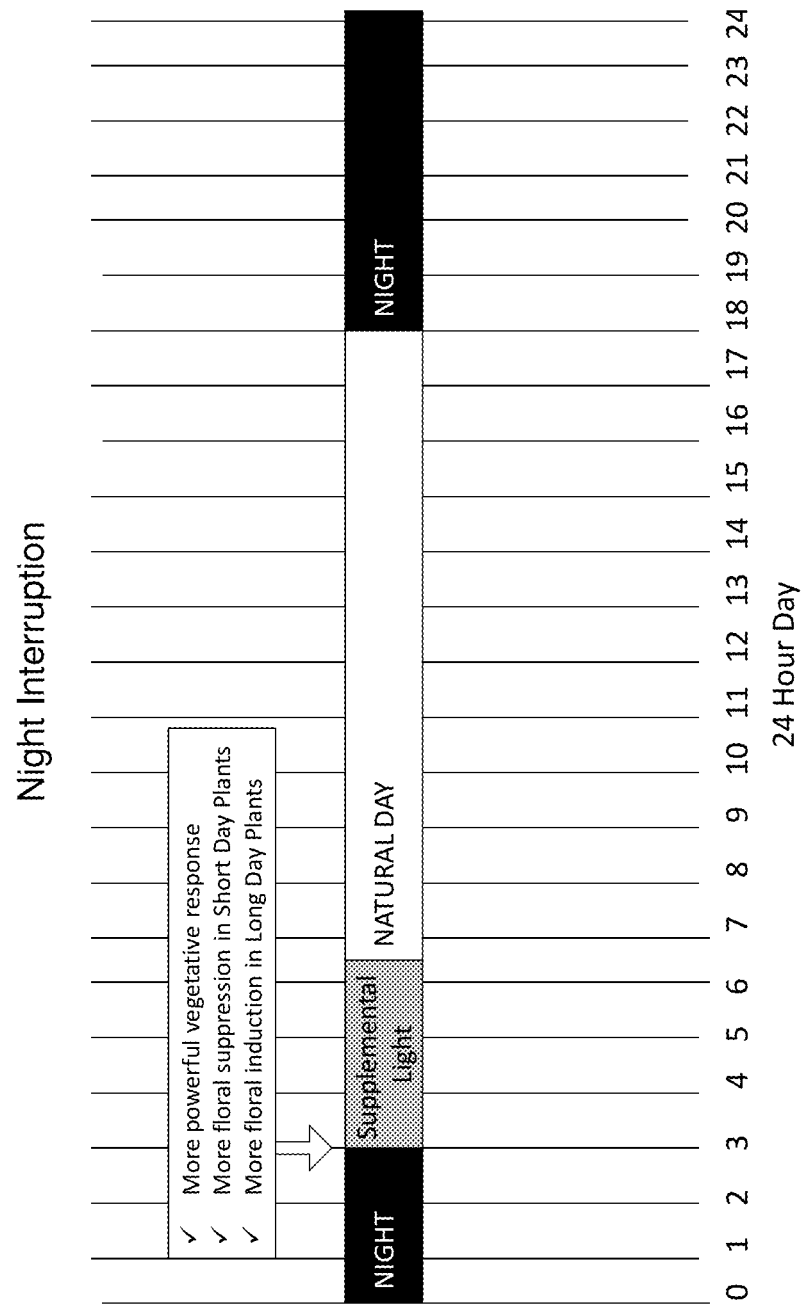
FIG. 2: Shows a graph demonstrating that the floral induction treatment induction utilizes a night-interruption application of supplemental photoperiod (pre-dawn) to provide a stronger vegetative response compared to extending photoperiod after sunset. This technique transitions the plant from darkness (night) to supplemental light, to natural day.

Night interruption of soy plants was performed by way of a timer that turned on a supplemental light canopy for a certain number of hours before natural sunrise. As shown in FIG. 2, results demonstrated that night interruption of photoperiod in the field provided greater control over the vegetative response in a plant compared to extending photoperiod after sunset.

Example 3

Manipulation of Yield and Cycle Length for Soybean Plants

This example describes a method for manipulating vegetative and flowering responses in soybean, a normally short day plant, with external signals for increasing seed yield and manipulating flowering time. The methods resulted in a consistent high yield phenotype and reduced cycle time. Three factors were manipulated in order to a correct balance of opposing vegetative and reproductive pathways: (1) Strength and persistence of initial reproductive dose (the floral induction treatment); (2) Strength of the non-induction (vegetative) signal after initiations of flowering; and (3) Relative maturity of the soybean germplasm.

Breeding facilities in southern latitudes were used for the following experiments, where the natural photoperiod causes early flowering in most maturity groups. Night length in these locations ranges from 10 hours to 14 hours throughout the season. Soy plants are entrained to the naturally short days and supplemental lights must compete against this entrainment.

Soybean seeds were planted on March 14 at 3 seeds per foot and allowed to germinate and grow under long-day conditions with a 20-hour photoperiod until the plants reached the V1 stage, when the first set of tri foliate leaves were unfolded. Lights were provided to the plants with the use of 1,000-watt metal halide portable light towers placed over the plants. The lighting was provided to the plants before dawn rather than after sunset.

Following the long day conditions, the V1 plants were then grown under floral induction treatment conditions (no artificial lighting, i.e, natural short day lengths) for a period of 10 days, after which time the plants were then grown under an 18-hour photoperiod for 14 days, and then under a 16-hour photoperiod for 16 days with the use of artificial lighting. The post floral induction treatment photoperiod was decreased to 16 hours from 18 hours by the grower to achieve more flowering response in this example. To obtain the necessary photoperiod, artificial lights and natural sunlight were used as described above.

Figure 3:
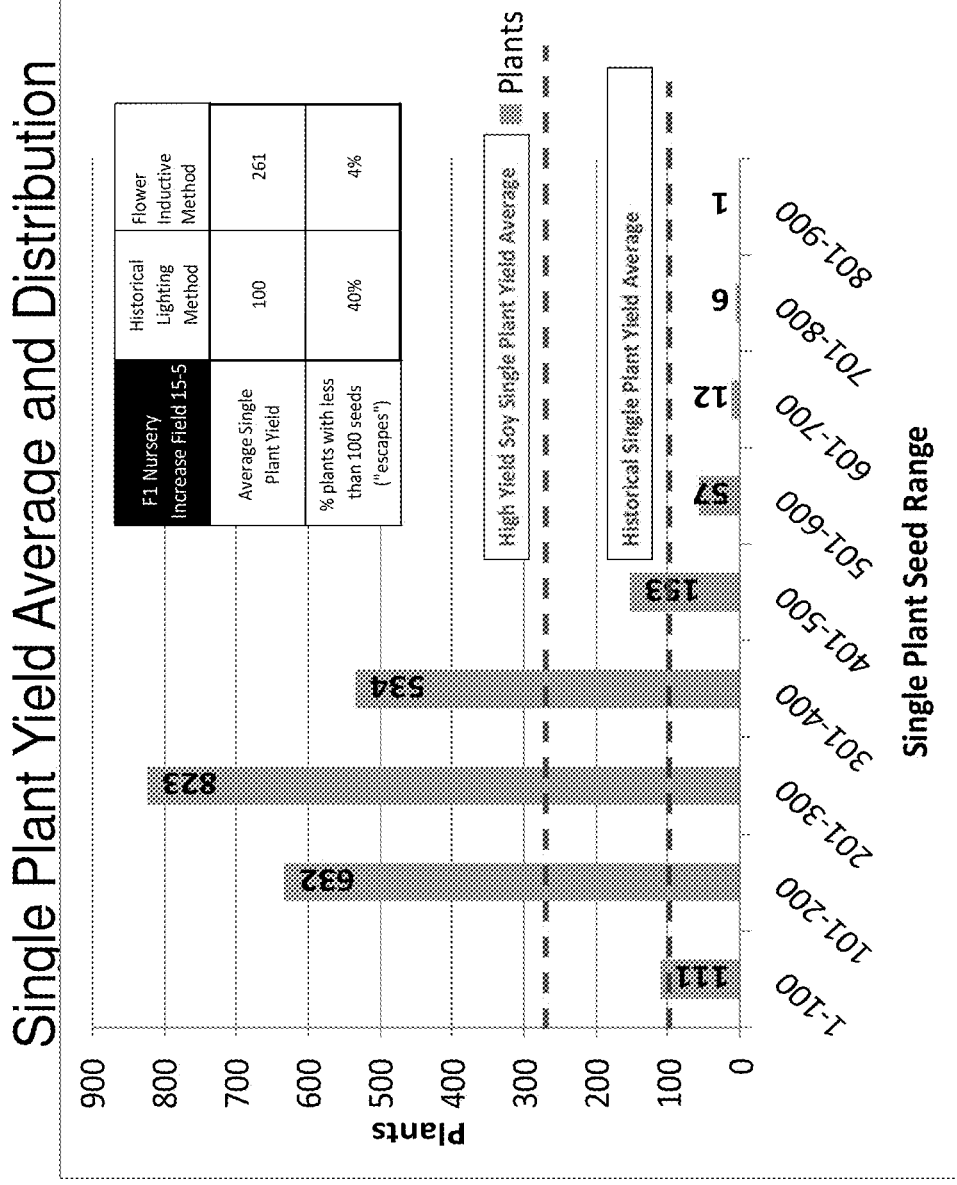
FIG. 3: This chart shows single-plant yield averages and distribution from 2,329 plants grown in a field after floral induction treatment. Average yield was 262 seeds per plant vs 100 for the historical yield metric in the same cycle time. In addition, the number of floral induction treated plants that did not meet the minimum yield target of 100 seeds ("escapes") was only 4% compared to 40% of plants not meeting the minimum yield target under historical methods.

The plants were harvested on July 5, 113 days after planting. This plant growth cycle was 7 days shorter than for plants grown under "normal" lighting. In addition, plants grown under the method exhibited a significant yield advantage, with the average yield being 464.8 seeds per single plant selection (FIG. 3) with 96% of the plants having greater than 100 seeds. Reducing plant density appears to result in increased yield potential with such methods vs. historical lighting practices at the same reduced density. Prior to using the described lighting methods, the yields of plants grown under typical lighting conditions average between 100-150 seeds per SPS with only 60% of the plants having greater than 100 seeds.

Example 4

Manipulation of Yield and Cycle Length for Soybean Plants

Figure 4:
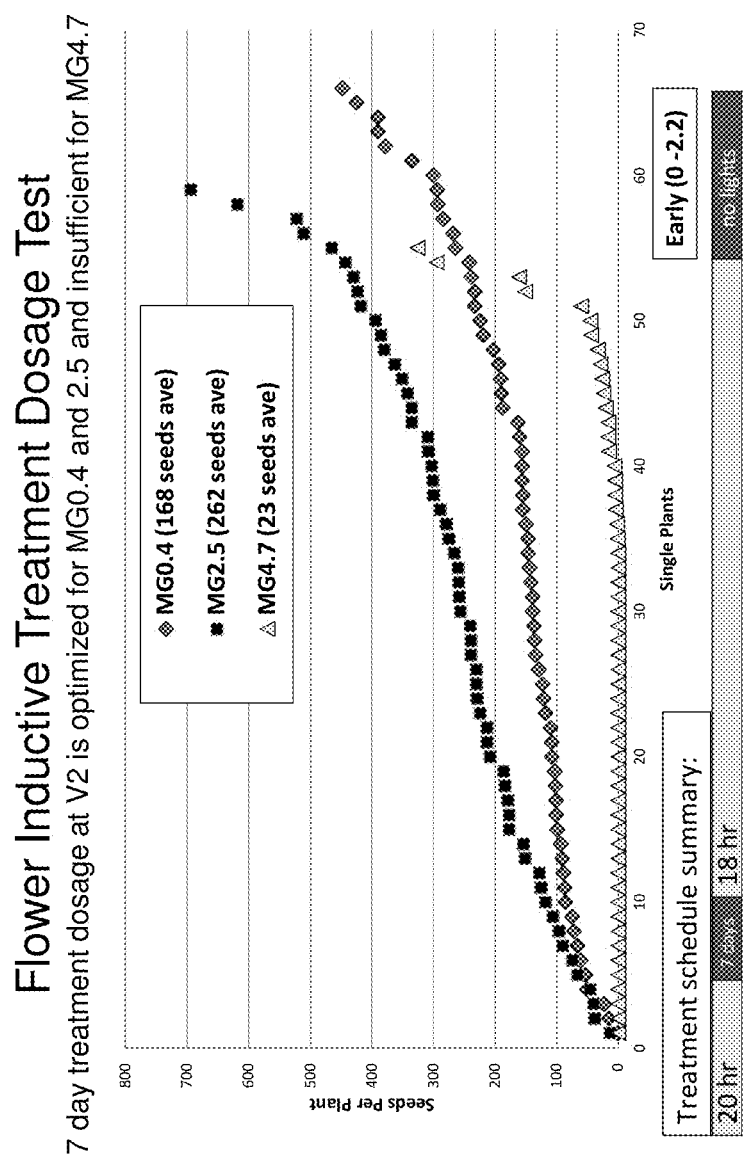
FIG. 4: Shows a test demonstrating that the floral induction treatment dosage has been customized for specific maturity groups and the yield response cannot be obtained without sufficient dosage. In this example, a 7-day floral induction treatment was sufficient to induce the increased yield response in maturity 0 and 2.5 but not in maturity 4.7 when returned to the 18-hour vegetative photoperiod.

The results of a floral induction treatment dosage test are shown in FIG. 4. Soybean seeds were planted on April 5 at 3 seeds per foot and allowed to germinate and grow under long-day conditions with a 20-hour photoperiod until the plants reached the V2 stage, when the first trifoliate leaf was fully expanded. Lights were provided to the plants with the use of 1,000-watt metal halide portable light towers placed over the plants. The photoperiod was extended by providing artificial light before dawn.

Following the long day conditions, the V2 plants were then grown under eSDI conditions (no artificial lighting, i.e, natural short day lengths) for a period of 7 days, after which time the plants were then grown under an 18-hour photoperiod for 35 days, and then under a 16-hour photoperiod for 7 days. To obtain the desired photoperiod, artificial lights and natural sunlight were used as described above.

Figure 5:
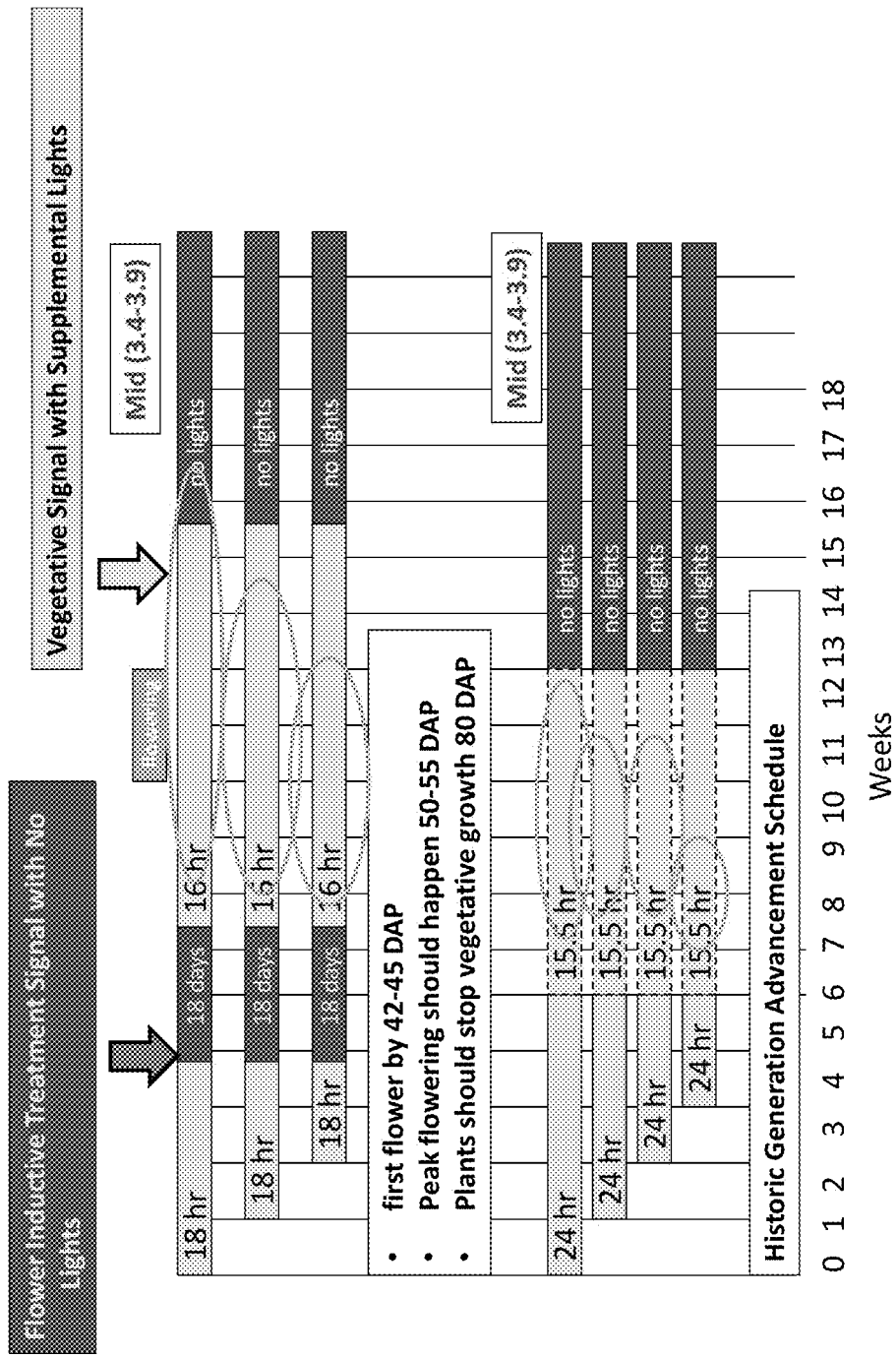
FIG. 5: Shows a treatment schematic of floral induction treatment application at the juvenile phase to induce early flowering for crossing block. Treatment is imposed at a fixed time, and each planting date will have a different developmental stage of plant during floral induction treatment. This creates a different dosage effect on plants in each planting date, which allows use of more light after floral induction treatment to increase flowering duration. The historical method uses the vegetative signal to delay flowering and this shortens the flowering phase compared to the floral induction treatment method.
Figure 6:
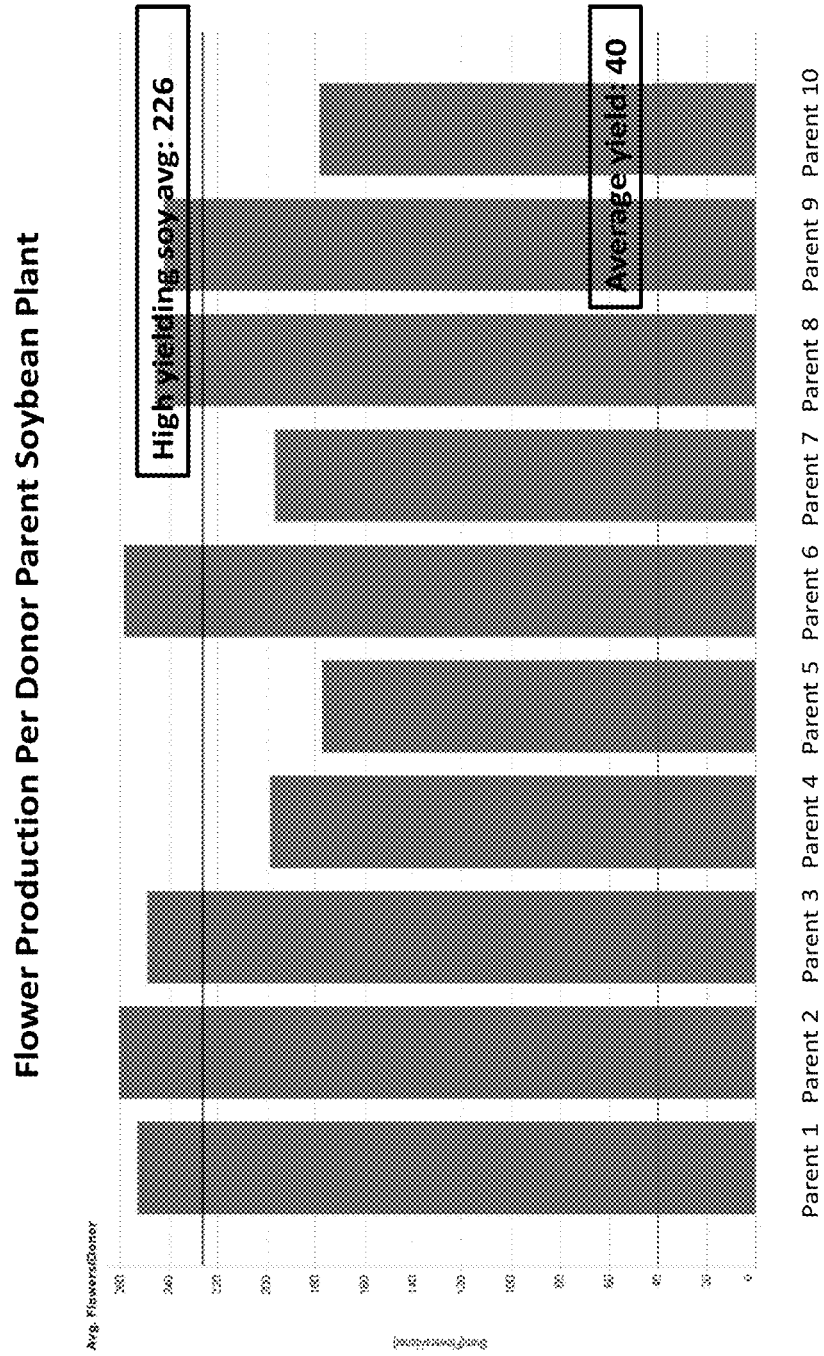
FIG. 6: Shows a graph of flower production per donor parent soybean plant. Historically, 40 flowers per donor parent plant were used. The invention described herein, increases flower production per donor parent soybean plant to assist with making cross pollinations. An average of 226 flowers per donor parent soybean plant was achieved, corresponding a 565% increase in production.

The plants were harvested on Aug. 2, 2012, 119 days after planting. Plants grown under the described method exhibited an extremely high yield phenotype for the cycle length, with the average yield being 510.7 seeds per single plant selection (SPS) (FIGS. 5-7).

Example 5

Synchronization of Flowering Times

Using the methods as described herein, early flowering was induced by exposure of field-grown plants to naturally short days found in southern latitudes and controlling the strength of flowering with the duration of the floral induction treatment period. After the floral reproductive dose was established, a vegetative signal was delivered with specific amounts of low intensity supplemental light. The key parameters of the method may be changed based on maturity group and project needs. In this manner, flowering times can be synchronized between two more plant varieties to be crossed, avoiding complicated planting schemes needed to permit simultaneous fertility of parents to be used as males and females in a given cross, particularly in the case of varieties with different maturities.

The eSDI method provides growers more capability to force and therefore to coordinate flowering, due to the sensitivity of juvenile plants to short day conditions (FIG. 5). In addition, the method allows for a prolonged duration of flowering, more flowers per internode, higher quality flowers, less shading of flowering internodes, and reduced short-day triggered pod abscission after hand pollination. Finally, the method greatly increases the supply of male donor flowers to be used in a pollen preservation program in which flowers from the male parent are collected, frozen at $-80°$ C. on desiccant, and used in the field later for hand pollinations.

Example 6

Increase in Flower Production of Parent Donor in MABCs

Growing plants using the methods described herein resulted in an increase in flower production of 560% in donor lines in a backcross model over traditional soybean breeding with standard growth conditions (FIG. 6). When the best selected donor plants were used for breeding, the resulting progeny plants showed a higher percentage of recurrent parent recovery in conversions.

The method used to grow soybean plants described in the above examples produced enough seed to skip the F1BC2 generation completely, thereby saving time and resources (FIG. 7). This allows faster advancements of traits in breeding programs. Increased single plant yields will also reduce the need for F1 seed since more F2 seed can be produced and homozygous lines fixed.

Example 7

Floral Induction Treatment for Mega-Maturities

Tables 1, 2 and 3 show floral induction treatment optimized for certain mega-maturity groups. Maturity group has a major effect on vegetative capability and persistence of the floral induction treatment dose with later groups requiring more floral induction and shorter vegetative photoperiods. If there is more than one mega-maturity under one light tower, then a compromised treatment can be used with the understanding that results will not be optimal. The most effective vegetative signal for balancing the floral induction dose to result in an increased yield appears to be equivalent to or slightly greater than the adapted maximum non-induction photoperiod for each maturity group. For example, a plant at maturity group (MG) 3.5 grown at 38° North latitude will receive about a 16-hour photoperiod on the June 21st, the longest day of the year. In controlled environments, MG3.5 is best grown under a 16-18 hour photoperiod after the floral induction treatment dose is established. The floral-repressive signal must be correctly balanced with the strength of the floral induction treatment dose and maturity group. A high vegetative signal:low floral induction treatment dose ratio will result in excessive vegetative growth, extended cycle time, and reduced yield. Conversely, a high floral induction treatment dose:low vegetative signal ratio will result in early maturity, reduced internode production, and reduced yield. Thus, the supplemental photoperiod appears to be competing with the natural day-length signal, which is tracked by the plant's circadian rhythm and photoreceptors in the leaves. In other words, the plant receives an induction signal when grown during seasonally short days despite being grown in a non-induction supplemental photoperiod. This natural diurnal induction can be countered by reducing the initial floral induction treatment dose or by employing a longer post-flowering photoperiod. The floral-repressive photoperiod may also be supplemented before the natural dawn (dark-to-light transition) rather than after sunset, resulting in a greater response in a plant than a photoperiod extension provided after sunset.

In order to address appropriate floral induction treatment conditions, maturity groups were further classified into mega-maturity groups as shown in Tables 1-3 below.

TABLE 1

Conditions for full cycle growth of mega-maturity groups
Phase I Floral Induction Treatment for Mega-Maturities
Generation Advancement: Full Cycle Method: 250 seeds in 120 Days

INDETERMINATE

| Mega-Group | Relative Maturity | Photoperiod Emergence --> V1 | Floral Induction Duration @ V2 | Photoperiod End of treatment --> R4 | Photoperiod R4--> Maturity |
|---|---|---|---|---|---|
| 1 - Early | 0-2.2 | 18 days @ 20 hrs | 10 days no lights | 47 days @ 18 hrs | End Lights @ 75 DAP |
| 2 - Mid-Early | 2.3-3.3 | 18 days @ 18 hrs | 14 days no lights | 43 days @ 16 hrs | End Lights @ 75 DAP |
| 3 - Mid | 3.4-3.9 | 18 days @ 18 hrs | 18 days no lights | 39 days at 16 hrs | End Lights @ 75 DAP |
| 4 - Mid-late | 4.0-5.2 | 18 days @ 16 hrs | 21 days no lights | 36 days @ 15 hrs | End Lights @ 75 DAP |

DETERMINATE

| Mega-Group | Relative Maturity | Photoperiod Emergence--> V3 | Floral Induction Duration @ V4 | Photoperiod End of treatment --> R4 | Photoperiod R4 --> Maturity |
|---|---|---|---|---|---|
| 5 - Late | 5.3-7.6 | 24 days @ 15 hrs | 21 days no lights | 30 days @ 15 hrs | End Lights @ 75 DAP |
| 6 - Very Late | 7.7-8.2 | 24 days @ 14 hrs | 21 days no lights | 30 days @ 14 hrs | End Lights @ 75 DAP |

TABLE 2

Conditions for rapid cycle growth of mega-maturity groups
Phase I Floral Induction Treatment for Mega-Maturities
Generation Advancement: Rapid Cycle Method: 100 seeds in 90 Days

INDETERMINATE

| Mega-Group | Relative Maturity | Photoperiod Emergence --> V1 | Floral Induction Duration @ V1 | Photoperiod End of treatment --> R4 | Photoperiod R4--> Maturity |
|---|---|---|---|---|---|
| 1 - Early | 0-2.2 | 12 days @ 20 hrs | 10 days no lights | 38 days @ 18 hrs | End Lights @ 60 DAP |
| 2 - Mid-Early | 2.3-3.3 | 12 days @ 18 hrs | 14 days no lights | 34 days @ 16 hrs | End Lights @ 60 DAP |
| 3 - Mid | 3.4-3.9 | 12 days @ 18 hrs | 18 days no lights | 30 days at 16 hrs | End Lights @ 60 DAP |
| 4 - Mid-late | 4.0-5.2 | 12 days @ 16 hrs | 21 days no lights | 27 days @ 15 hrs | End Lights @ 60 DAP |

DETERMINATE

| Mega-Group | Relative Maturity | Photoperiod Emergence--> V3 | Floral Induction Duration @ V3 | Photoperiod End of treatment-> R4 | Photoperiod R4 --> Maturity |
|---|---|---|---|---|---|
| 5 - Late | 5.3-7.6 | 21 days @ 15 hrs | 21 days no lights | 18 days @ 14 hrs | End Lights @ 60 DAP |
| 6 - Very Late | 7.7-8.2 | 21 days @ 14 hrs | 21 days no lights | 18 days @ 13 hrs | End Lights @ 60 DAP |

TABLE 3

Conditions for synchronization of flowering
Phase I Floral Induction Treatment for Mega-Maturities
Crossing Blocks: Full Cycle with 3 Planting Dates

INDETERMINATE

| Mega-Group | Relative Maturity | Planting Date | Photoperiod Emergence --> Start | Duration @ Range V1-4 | Photoperiod End of Treatment --> R4 | Photoperiod R4 to maturity |
|---|---|---|---|---|---|---|
| 1 - Early | 0-2.2 | #1 | 25 days @ 20 hrs | 10 days no lights | 55 days @ 18 hrs | End Lights @ 90 DAP |
| | | #2 (#1 + 7 days) | 18 days @ 20 hrs | 10 days no lights | 55 days @ 18 hrs | End Lights @ 83 DAP |
| | | #3 (#1 + 14 days) | 11 days @ 20 hrs | 10 days no lights | 55 days @ 18 hrs | End Lights @ 76 DAP |
| 2 - Mid-Early | 2.3-3.3 | #1 | 25 days @ 18 hrs | 14 days no lights | 51 days @ 16 hrs | End Lights @ 90 DAP |
| | | #2 (#1 + 7 days) | 18 days @ 18 hrs | 14 days no lights | 51 days @ 16 hrs | End Lights @ 83 DAP |
| | | #3 (#1 + 14 days) | 11 days @ 18 hrs | 14 days no lights | 51 days @ 16 hrs | End Lights @ 76 DAP |
| 3 - Mid | 3.4-3.9 | #1 | 25 days @ 18 hrs | 18 days no lights | 47 days at 16 hrs | End Lights @ 90 DAP |
| | | #2 (#1 + 7 days) | 18 days @ 18 hrs | 18 days no lights | 47 days at 16 hrs | End Lights @ 83 DAP |
| | | #3 (#1 + 14 days) | 11 days @ 18 hrs | 18 days no lights | 47 days at 16 hrs | End Lights @ 76 DAP |
| 4 - Mid-late | 4.0-5.2 | #1 | 21 days @ 16 hrs | 21 days no lights | 48 days @ 15 hrs | End Lights @ 90 DAP |
| | | #2 (#1 + 7 days) | 14 days @ 16 hrs | 21 days no lights | 48 days @ 15 hrs | End Lights @ 83 DAP |
| | | #3 (#1 + 14 days) | 7 days @ 16 hrs | 21 days no lights | 48 days @ 15 hrs | End Lights @ 76 DAP |

DETRMINATE

| Mega-Group | Relative Maturity | | Photoperiod Emergence --> Start | Duration @ Range V2-5 | Photoperiod End of Treatments–> R4 | Photoperiod R4 to maturity |
|---|---|---|---|---|---|---|
| 5 - Late | 5.3-7.6 | #1 | 28 days @ 15 hrs | 18 days no lights | 44 days @ 15 hrs | End Lights @ 90 DAP |
| | | #2 (#1 + 7 days) | 21 days @ 15 hrs | 21 days no lights | 44 days @ 15 hrs | End Lights @ 86 DAP |
| | | #3 (#1 + 14 days) | 14 days @ 15 hrs | 21 days no lights | 44 days @ 15 hrs | End Lights @ 79 DAP |
| 6 - Very Late | 7.7-8.2 | #1 | 28 days @ 14 hrs | 21 days no lights | 41 days @ 14 hrs | End Lights @ 90 DAP |
| | | #2 (#1 + 7 days) | 21 days @ 14 hrs | 21 days no lights | 41 days @ 14 hrs | End Lights @ 83 DAP |
| | | #3 (#1 + 14 days) | 14 days @ 14 hrs | 21 days no lights | 41 days @ 14 hrs | End Lights @ 76 DAP |

Example 8

Optimizing Lighted Soybean Field Nurseries Supplemental Light Canopy (SLC) and Field Area Design The typical lighted nursery field area used was equal to two adjacent 5000 ft$^2$ (465 m$^2$) fields with maximum dimensions of 100 feet wide by 50 feet deep. The supplemental light canopy (SLC) used was a portable light tower comprised of four 1000-W metal halide bulbs with reflectors, diesel engine, boom, electrical system, cabinet, and control panel including timer. Any SLC with correct intensity output and area coverage would be expected to work such as fixed stadium lights or solar-charged battery powered lights. Two 1000-W metal halide bulbs with reflectors were the minimum number used to treat each 5000 ft$^2$ field. The SLC was adjusted to a height of 12-16 ft and the bulb reflectors was positioned at 45-60° angles from the boom depending on field area and soybean canopy height.

Example 9

Yield and Cycle Time Manipulation Across Broad Soybean Maturities

This example describes the rapid advancement of a number of different soybean later maturity groups when grown in southern locations using the conditions described in the above examples. Typically, when soybeans of maturity groups which are not adapted for southern latitudes are grown in southern locations, such soybeans can achieve a cycle time as short as 90 days but will only yield approximately 50 seeds per plant.

Soybean plants having maturity groups not adapted for southern latitudes (see Table 4, below) were grown in southern locations using supplemental photoperiod, whereby the plants received an induction signal followed by modulation of the length of the photoperiod post-induction. The floral induction signal in the later maturity groups was consistent with ensuring persistent flowering during the period of long vegetative growth. Plants grown under such conditions obtained desired cycle times of below 100 days. Table 4 illustrates the results and shows that yields were increased by 2.3 to 7-fold.

TABLE 4

Conditions for increased yield and cycle time in mega maturity soybean

| Maturity Group | Photoperiod Emergence --> V1 | Floral Induction Duration @ V1-V2 | Photoperiod post floral-induction | Photoperiod End of Treatment --> R4 | Cycle Time (Planting to Harvest) | Seed Yield Per Plant |
|---|---|---|---|---|---|---|
| 0.7-1.9 | 12 days @ 20 hrs | 11 days no supplemental light | 18-->16 hrs | 45 days | 98 days | 265 |

TABLE 4-continued

Conditions for increased yield and cycle time in mega maturity soybean

| Maturity Group | Photoperiod Emergence --> V1 | Floral Induction Duration @ V1-V2 | Photoperiod post floral-induction | Photoperiod End of Treatment --> R4 | Cycle Time (Planting to Harvest) | Seed Yield Per Plant |
|---|---|---|---|---|---|---|
| 1.5-2.7 | 12 days @ 18 hrs | 14 days no supplemental light | 16-->14 hrs | 49 days | 95 days | 328 |
| 2.1-3.8 | 12 days @ 18 hrs | 14 days no supplemental light | 16-->14 hrs | 45 days | 97 days | 293 |
| 2.3-3.8 | 12 days @ 18 hrs | 17 days no supplemental light | 16-->14 hrs | 44 days | 99 days | 364 |
| 4.1-5.7 | 21 days @ 16 hrs | 16 days no supplemental light | 14 hrs | 36 days | 92 days | 368 |
| 4.1-7.9 | 21 days @ 15 hrs | 21 days no supplemental light | 15 hrs | 44 days | 93 days | 289 |

What is claimed is:

1. A method for increasing seed yield in a field-grown soybean plant, the method comprising:
   (a) growing the soybean plant in a field under vegetative growing conditions;
   (b) exposing the soybean plant to a photoperiodic floral induction treatment such that a flowering response is initiated; and
   (c) returning the soybean plant to vegetative growing conditions,
   wherein the vegetative growing conditions of one or both of part (a) and (c) comprise from about 14 to about 18 hours of light per day and wherein the vegetative growing conditions are provided by exposing the soybean plant to artificial lighting comprising an intensity of 2 to 150 µmoles/m·s before sunrise or after sunset or a combination thereof.

2. The method of claim 1, wherein the artificial lighting is provided to the soybean plant before sunrise.

3. The method of claim 1, wherein the floral induction treatment of part (b) further comprises about 11 to about 13 hours of darkness per night.

4. The method of claim 1, wherein the floral induction treatment of part (b) is maintained for a period of about 7 to about 28 days.

5. The method of claim 1, wherein the floral induction treatment of part (b) is initiated at a growth stage of from about VE to about V4.

6. The method of claim 1, wherein the artificial lighting comprises an intensity of at least 5 µmoles/m·s.

7. The method of claim 6, wherein the artificial lighting comprises an intensity of less than 100 µmoles/m·s.

8. The method of claim 7, wherein the artificial lighting comprises an intensity of at least 10 µmoles/m·s.

9. The method of claim 7, wherein the artificial lighting comprises an intensity of at least 15 µmoles/m·s.

10. The method of claim 7, wherein the artificial lighting comprises an intensity of at least 25 µmoles/m·s.

11. The method of claim 7, wherein the artificial lighting comprises an intensity of less than 50 µmoles/m·s.

12. The method of claim 7, wherein the artificial lighting comprises an intensity of less than 75 µmoles/m·s.

13. The method of claim 6, wherein the artificial lighting comprises an intensity of less than 50 µmoles/m·s.

14. The method of claim 6, wherein the artificial lighting comprises an intensity of less than 75 µmoles/m·s.

15. The method of claim 6, wherein the artificial lighting comprises an intensity of less than 125 µmoles/m·s.

16. The method of claim 1, comprising growing the soybean plant under conditions that restrict vegetative growth and enhance flowering.

17. The method of claim 1, wherein one or both of part (a) and part (c) comprise providing about 1, about 2, about 3, about 4, or about 5 hours of artificial light per day before sunrise.

18. The method of claim 1, wherein the floral induction treatment of part (b) comprises covering the soybean plant to block ambient light.

19. The method of claim 1, wherein the seed yield is increased by 2.3 to 7-fold relative to the seed yield of a soybean plant that was not subjected to steps (a)-(c).

20. The method of claim 1, wherein the artificial lighting comprises an intensity of less than 25 µmoles/m·s.

21. The method of claim 1, wherein the artificial lighting comprises an intensity of less than 50 µmoles/m·s.

22. The method of claim 1, wherein the artificial lighting comprises an intensity of less than 75 µmoles/m·s.

23. The method of claim 1, wherein the artificial lighting comprises an intensity of less than 100 µmoles/m·s.

24. The method of claim 1, wherein the artificial lighting comprises an intensity of less than 125 µmoles/m·s.

25. A method for increasing flowering in a plurality of field-grown soybean plants, the method comprising:
   (a) initiating growth of a plurality of soybean plants under vegetative growing conditions;
   (b) exposing the plurality of soybean plants to a photoperiodic floral induction treatment to initiate flowering; and
   (c) returning the plurality of soybean plants to vegetative growing conditions,
   wherein the vegetative growing conditions of one or both of part (a) and (c) comprise from about 14 to about 18 hours of light per day and wherein the vegetative growing conditions are provided by exposing the soybean plants to artificial lighting comprising an intensity of 2 to 150 µmoles/m·s before sunrise or after sunset or a combination thereof.

26. The method of claim 25, wherein the artificial lighting is provided before sunrise.

27. The method of claim 25, wherein the artificial lighting comprises an intensity of at least 5 μmoles/m·s.

28. The method of claim 25, wherein the artificial lighting comprises an intensity of less than 100 μmoles/m·s.

29. The method of claim 25, wherein the plurality of soybean plants comprises plants of at least two different genotypes.

30. The method of claim 29, wherein the method synchronizes the flowering time of said plants of at least two different genotypes to permit crossing.

31. The method of claim 25, wherein the floral induction treatment of part (b) comprises about 11 to about 13 hours of darkness per night.

32. The method of claim 25, wherein the floral induction treatment of part (b) is maintained for a period of about 7 to about 28 days.

33. The method of claim 25, wherein at least one soybean plant is at a growth stage of from about VE to about V4.

34. The method of claim 25, wherein one or both of part (a) and part (c) comprise providing about 1, about 2, about 3, about 4, or about 5 hours of artificial light before sunrise.

35. The method of claim 25, further comprising growing the plurality of soybean plants under conditions that restrict vegetative growth and enhance flowering.

36. The method of claim 25, wherein at least two of said plurality of field-grown soybean plants are planted at differing times.

37. The method of claim 25, wherein the floral induction treatment of part (b) comprises covering the plurality of soybean plants to block ambient light.

38. A method for increasing seed yield in a field-grown soybean plant, the method comprising:
(a) exposing a soybean plant in a field to vegetative growing conditions, wherein the vegetative growing conditions are provided by the use of artificial lighting before sunrise or after sunset or a combination thereof;
(b) exposing the plant to a floral induction treatment of 7-28 days in duration to initiate flowering, wherein said floral induction treatment is initiated at a growth stage of from about VE to about V4, and wherein said floral induction treatment comprises about 11 to about 13 hours of darkness per night; and
(c) returning the plant to vegetative growing conditions of 14-60 days in duration, wherein said vegetative growing conditions comprise providing artificial lighting before sunrise or after sunset or a combination thereof to expose the plant to from about 14 to about 18 hours of light per day, wherein the artificial lighting comprises an intensity of 2 to 150 μmoles/m·s.

39. The method of claim 38, wherein the artificial lighting comprises an intensity of at least 5 μmoles/m·s.

40. The method of claim 38, wherein the artificial lighting comprises an intensity of less than 100 μmoles/m·s.

41. The method of claim 38, wherein the seed yield is increased by 2.3 to 7-fold relative to the seed yield of a soybean plant that was not subjected to steps (a)-(c).

42. A method of growing a soybean plant in a field comprising:
(a) initiating growth of the soybean plant in a field;
(b) determining a natural photoperiod of the soybean plant;
(c) adjusting the photoperiod to which the soybean plant is exposed with an artificial light source before sunrise or after sunset or a combination thereof to produce a vegetative growing condition;
(d) growing the soybean plant in the field under vegetative growing conditions to a juvenile stage;
(e) exposing the soybean plant to a floral induction treatment, such that a flowering response is initiated;
(f) adjusting the photoperiod to which the soybean plant is exposed with the artificial light source before sunrise or after sunset or a combination thereof to produce a vegetative growing condition; and
(g) growing the soybean plant under vegetative growing conditions, wherein the artificial light source comprises an intensity of 2 to 150 μmoles/m·s.

43. A method of growing a soybean plant in a field comprising:
(a) initiating growth of the soybean plant in a field;
(b) determining a natural photoperiod of the soybean plant;
(c) growing the soybean plant under natural photoperiodic conditions to provide a floral induction treatment, such that a flowering response is initiated;
(d) adjusting the photoperiod to which the soybean plant is exposed with an artificial light source before sunrise or after sunset or a combination thereof to produce a vegetative growth condition; and
(e) growing the soybean plant under vegetative growing conditions, wherein the artificial light source comprises an intensity of 2 to 150 μmoles/m·s.

44. A method of growing a soybean plant comprising:
(a) initiating growth of the soybean plant in a field;
(b) determining a natural photoperiod of the soybean plant;
(c) growing the soybean plant under vegetative growing conditions;
(d) adjusting the photoperiod to which the soybean plant is exposed to provide a floral induction treatment, such that a flowering response is initiated; and
(e) returning the soybean plant to vegetative growing conditions, wherein the vegetative growing conditions are provided by exposing the soybean plant to artificial lighting comprising an intensity of 2 to 150 μmoles/m·s before sunrise or after sunset or a combination thereof.

* * * * *

UNITED STATES PATENT AND TRADEMARK OFFICE
CERTIFICATE OF CORRECTION

PATENT NO. : 11,122,753 B2
APPLICATION NO. : 14/207284
DATED : September 21, 2021
INVENTOR(S) : Ovadya et al.

Page 1 of 1

It is certified that error appears in the above-identified patent and that said Letters Patent is hereby corrected as shown below:

In the Claims

In Column 19, Line 39, Claim 1, delete "µmoles/ms" and insert --µmoles/m·s--

Signed and Sealed this
Twenty-first Day of November, 2023

Katherine Kelly Vidal
*Director of the United States Patent and Trademark Office*